US006761743B1

(12) United States Patent
Johnson

(10) Patent No.: US 6,761,743 B1
(45) Date of Patent: *Jul. 13, 2004

(54) ALIGNMENT DEVICE FOR A PROSTHETIC LIMB

(76) Inventor: Timothy Johnson, 453 Withers La., Walton, KY (US) 41094

( * ) Notice: Subject to any disclaimer, the term of this patent is extended or adjusted under 35 U.S.C. 154(b) by 0 days.

This patent is subject to a terminal disclaimer.

(21) Appl. No.: 09/937,390

(22) PCT Filed: Nov. 23, 1999

(86) PCT No.: PCT/US99/27859

§ 371 (c)(1),
(2), (4) Date: Sep. 24, 2001

(87) PCT Pub. No.: WO00/30572

PCT Pub. Date: Jun. 2, 2000

Related U.S. Application Data

(63) Continuation-in-part of application No. 09/199,240, filed on Nov. 24, 1998, now Pat. No. 6,206,932.

(51) Int. Cl.[7] .................................................. A61F 2/62
(52) U.S. Cl. ....................................................... 623/38
(58) Field of Search .............................. 623/27, 31–33, 623/36, 38, 57–58

(56) References Cited

U.S. PATENT DOCUMENTS

| 2,749,557 | A | 6/1956 | Riddle | 623/50 |
|---|---|---|---|---|
| 3,619,818 | A | 11/1971 | Collins | 623/57 |
| 3,659,294 | A | 5/1972 | Glabisezewski | |
| 4,547,913 | A | 10/1985 | Phillips | 623/27 |
| 4,822,363 | A | 4/1989 | Phillips | 623/27 |
| 4,969,911 | A | 11/1990 | Greene | 623/38 |
| 5,290,319 | A | 3/1994 | Phillips | 623/56 |
| 5,376,133 | A | 12/1994 | Gramnäs | 623/38 |
| 5,443,529 | A | 8/1995 | Phillips | 623/56 |
| 5,458,657 | A | * 10/1995 | Rasmusson | 623/38 |
| 5,529,576 | A | 6/1996 | Lundt et al. | 623/38 |

FOREIGN PATENT DOCUMENTS

DE 125956 1/1901 .................. 623/27

OTHER PUBLICATIONS

International Search Report, PCT/US99/27859.

* cited by examiner

Primary Examiner—David H. Willse
(74) Attorney, Agent, or Firm—Wood, Herron & Evans, LLP

(57) ABSTRACT

An alignment device (10) for a prosthetic limb (12) to provide angular movement of the prosthetic limb (12) in an anterior-posterior plane. The alignment device (10) includes a mounting mechanism (24) supported by a prosthetic socket (28), a prosthetic limb (12) operatively connected to the mounting mechanism (24), and an extendable and retractable positioning mechanism (84) operatively connected to the mounting mechanism (24) and the prosthetic limb (12). The prosthetic limb (12) is adapted to move angularly in the anterior-posterior plane upon extension or retraction of the positioning mechanism (84). A hinge connection (606, 610) may be provided between the prosthetic limb (12) and the mounting mechanism (602) to permit the prosthetic limb (12) to rotate about a hinge axis extending through the hinge connection (606, 610). Methods for aligning a prosthetic limb are also disclosed.

14 Claims, 9 Drawing Sheets

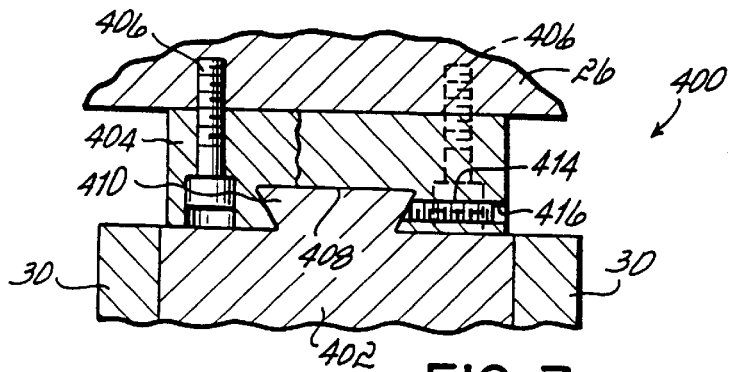
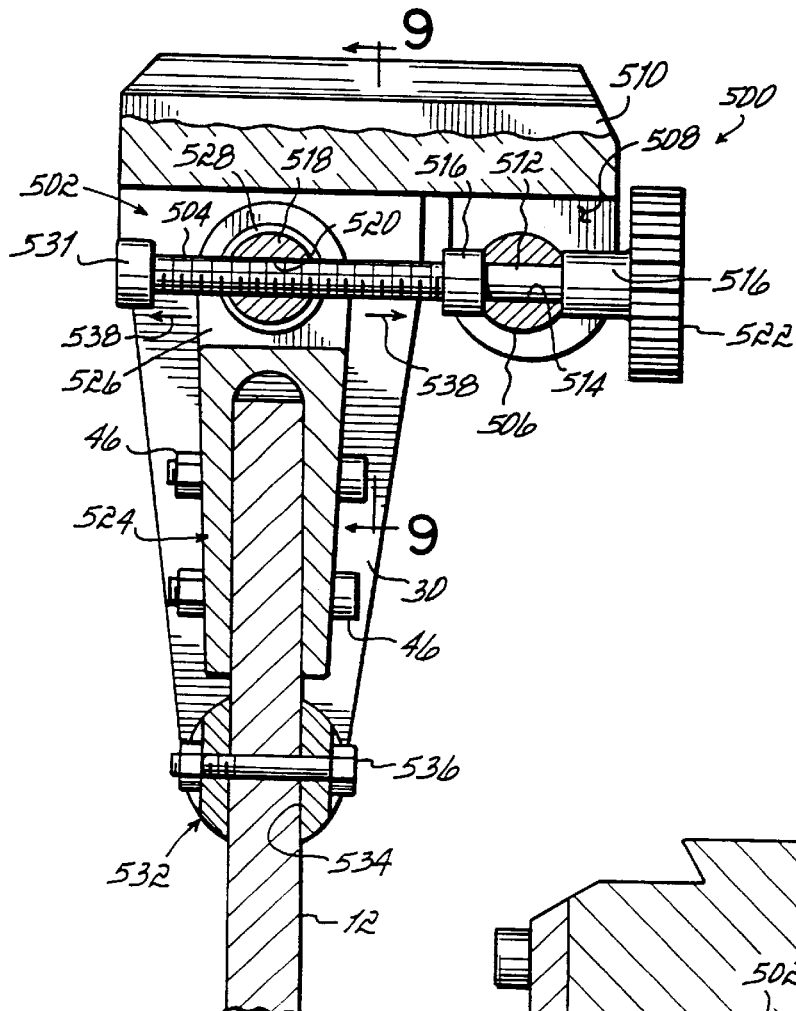
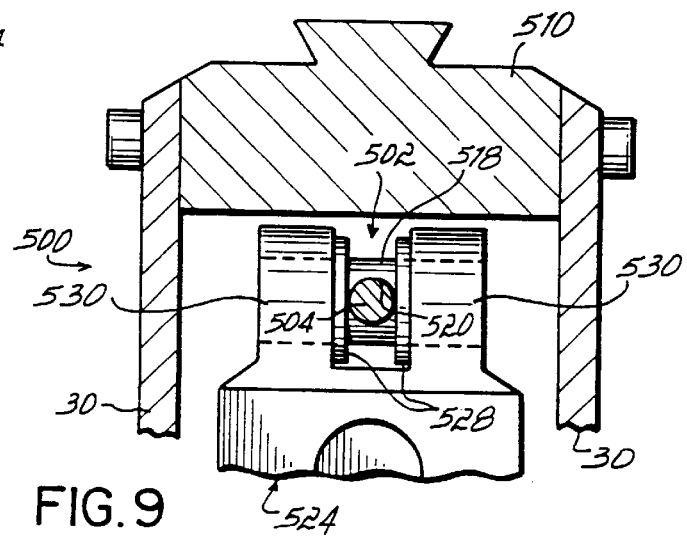

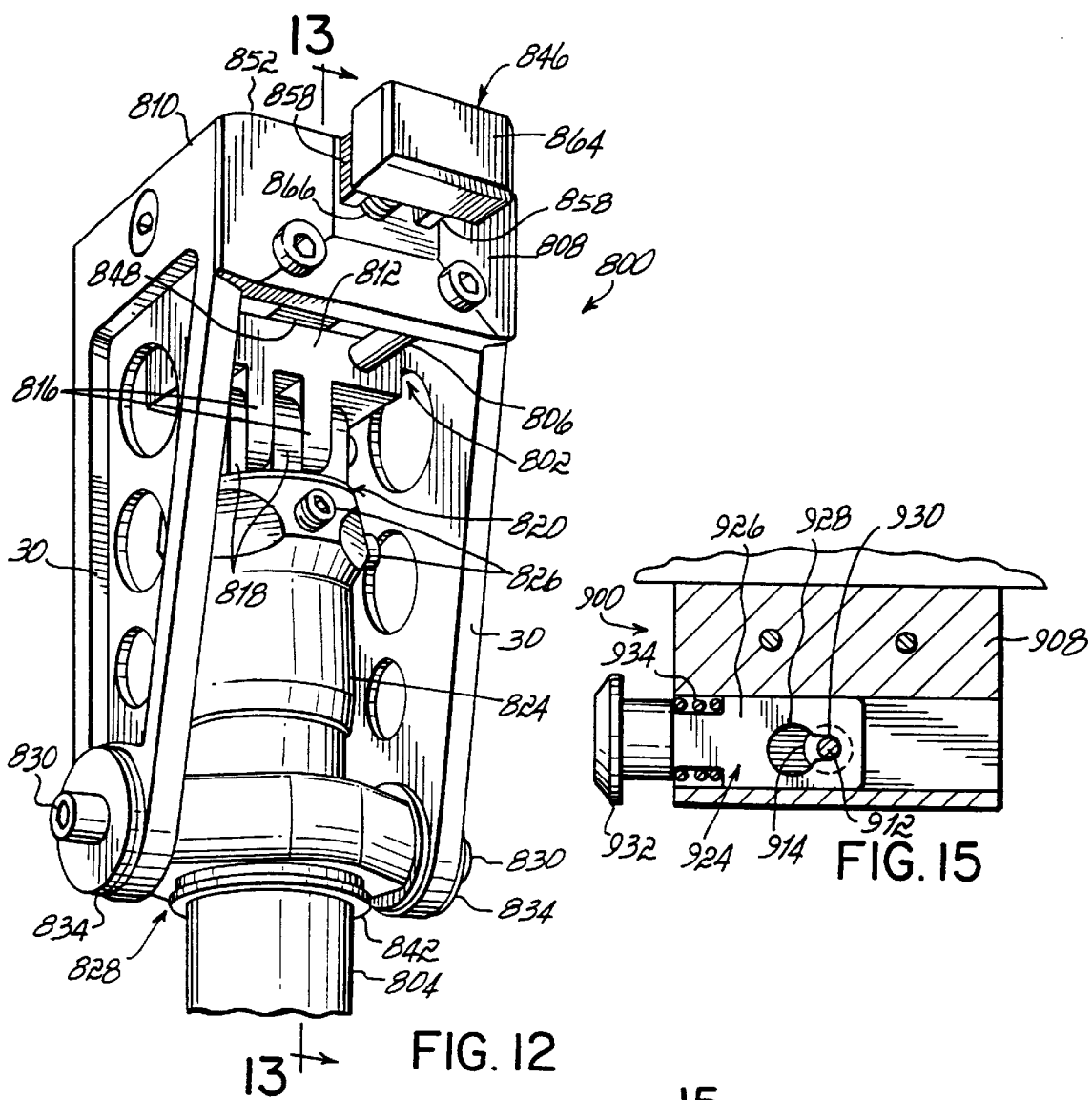
FIG. 12
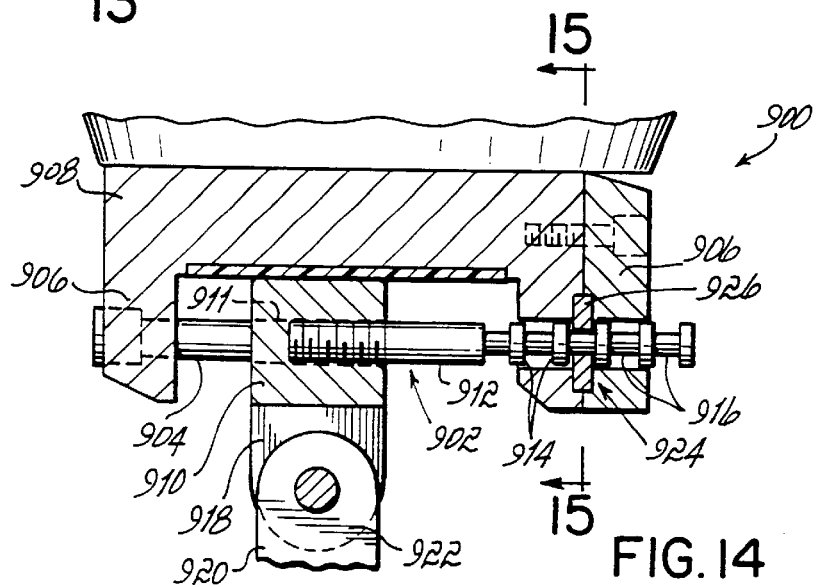
FIG. 14
FIG. 15

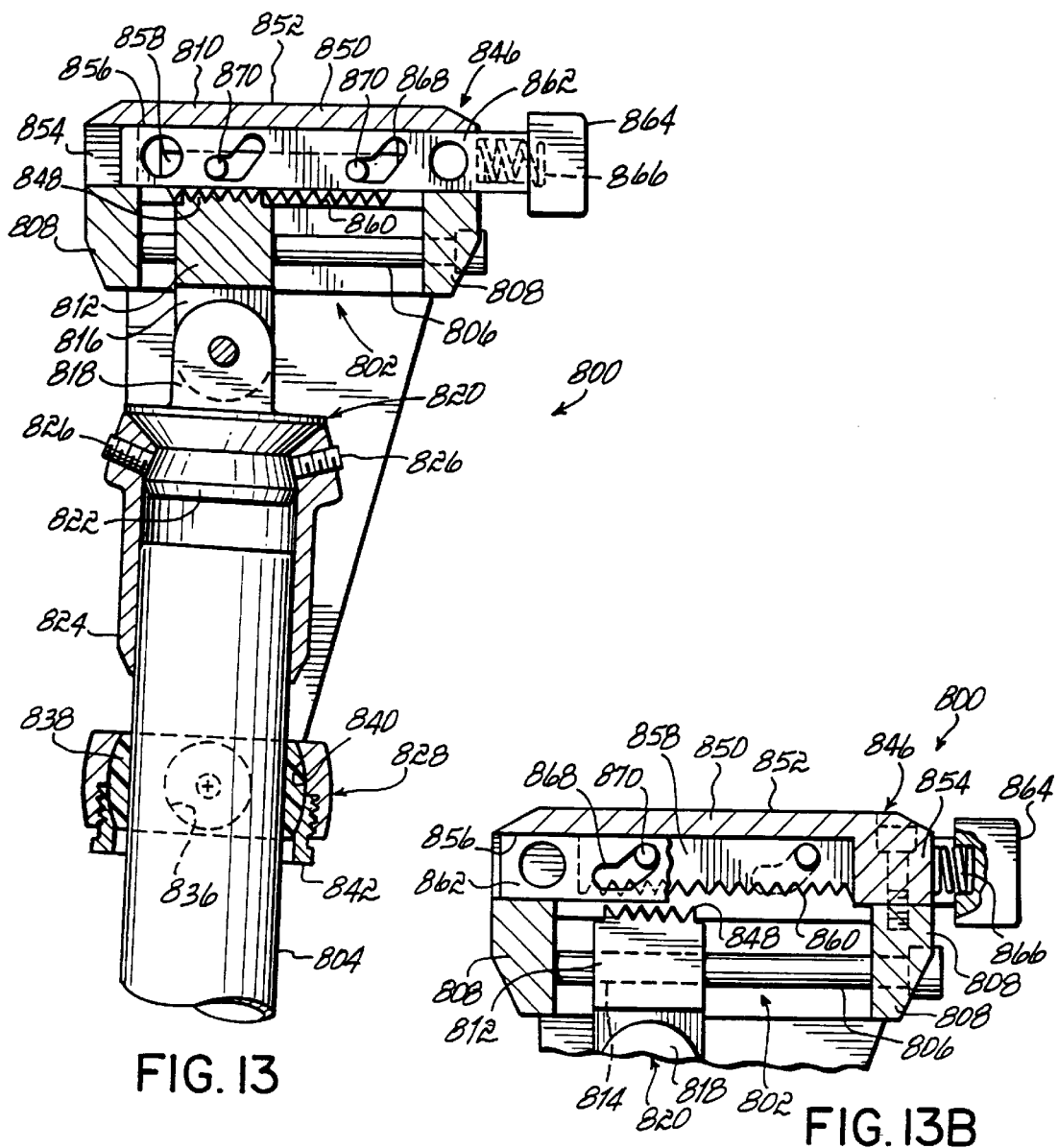
FIG. 13
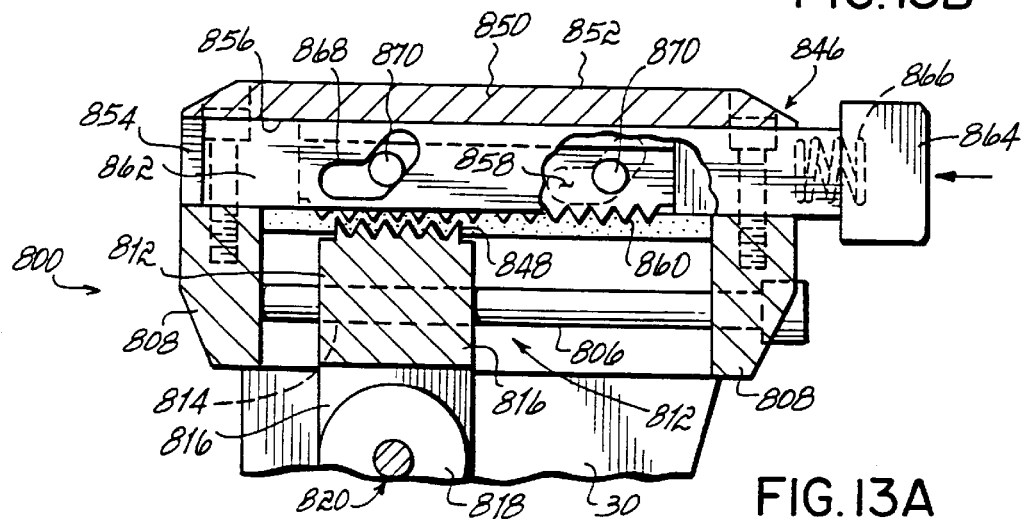
FIG. 13B
FIG. 13A

ALIGNMENT DEVICE FOR A PROSTHETIC LIMB

CROSS-REFERENCE

The present application is a continuation-in-part of my copending application U.S. Ser. No. 09/199,240, filed on Nov. 24, 1998, now U.S. Pat. No. 6,206,932, the disclosure of which is hereby incorporated by reference herein in its entirety.

FIELD OF THE INVENTION

The present invention relates generally to prosthetic devices and, more particularly, to an alignment device for providing angular adjustment of a prosthetic limb in forward and rearward directions to obtain a customized fit for the wearer.

BACKGROUND OF THE INVENTION

Various devices have been developed to provide alignment for prosthetic limbs, such as a prosthetic lower leg worn by a below-the-knee amputee. The limb is typically adjustably attached to a prosthetic knee socket for providing a rigid leg support. The alignment devices are designed to permit angular adjustment of the limb in a forward-rearward plane below the prosthetic knee socket to approximate the proper toe-to-heel pitch and gait for the wearer. Proper fit of the prosthetic limb is necessary for the full range of motion and activity of the wearer to avoid undesirable health risks, particularly in diabetic amputees that are susceptible to irritation in areas on and around the residual limb common to amputees. This irritation primarily results from improper loading on the rigid prosthetic knee socket that causes excessive pressure in areas of the residual limb.

In the past, alignment devices have been designed that mount between a lower end of a prosthetic socket and an upper end of a prosthetic limb. The prosthetic limb may include a leg portion and a leaf-spring foot portion. In general, the leg and foot portions of the prosthetic limb are rigid members, although some elastic energy absorbing members may be provided to help absorb shock as the wearer goes through conventional motions.

In one known alignment approach for prosthetic limbs, such as those of the laminated plate-type as disclosed in U.S. Pat. Nos. 4,547,913 and 4,822,363, the limb is attached to a mounting flange extending downwardly from the prosthetic knee socket. A prosthetist angularly aligns the limb in forward and rearward directions by inserting various angled wedge or shim adaptors between an upper end of the limb and a lower end of the mounting flange. Shim adaptors of varying angles are tested by the prosthetist until one providing the most favorable toe-to-heel pitch and gait for the wearer is identified.

In another known alignment approach, the prosthetic limb is connected to the prosthetic socket through a rotational joint, such as a rotatable socket adaptor or pair of sliding curved plates. During the custom fitting process, the prosthetist rotationally adjusts and aligns the prosthetic limb relative to the knee socket to the desired angular position for proper toe-to-heel pitch and gait. Typically, the alignment procedure requires multiple adjustments to the alignment device with adjustment tools.

In each of the alignment approaches described above, the wearer may be restricted to the toe-to-heel pitch set by the prosthetist after the custom fitting process, and the wearer may have limited ability to readily adjust the angular setting of the limb as may be desired, particularly when changing between shoes of different heel height. When the wearer does attempt to make an alignment adjustment, that adjustment may affect other adjustments already set on the prosthetic limb, thereby adding to the complexity of the adjustment process. To avoid making complex manual adjustments to the alignment device for accommodating shoes of different height, the wearer may insert padding, shims or other adjustment devices into the shoes which improves the fit but may not achieve the optimum toe-to-heel pitch and gait for the particular shoe. Alternatively, the wearer may simply decide to wear shoes of only one heel height.

Thus, there is a need for a prosthetic limb alignment device that is readily manually adjustable by the wearer to optimize the toe-to-heel pitch and gait of the wearer.

There is also a need for a prosthetic limb alignment device that is readily manually adjustable by the wearer to accommodate for shoes of different heel heights while providing the optimum toe-to-heel pitch and gait for the wearer.

There is yet another need for a prosthetic limb alignment device that may be readily manually adjusted by the wearer without requiring adjustment tools.

There is yet also a need for a prosthetic limb adjustment device that is readily manually adjustable without affecting other adjustments set on the prosthetic limb.

SUMMARY OF THE INVENTION

The present invention overcomes the foregoing and other shortcomings and drawbacks of alignment devices and methods heretofore known. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, an alignment device and method are provided for aligning a prosthetic limb worn by an amputee. The alignment device may be used in a below-the-knee amputation environment wherein it is mounted between a lower end of a prosthetic socket and an upper end of a prosthetic limb. The alignment device is particularly designed to provide angular alignment of the prosthetic limb in forward and rearward directions below the knee socket to optimize the toe-to-heel pitch and gait for the wearer as shoes of different height are worn. Other adjustments of the prosthetic limb relative to the prosthetic knee socket are also possible with the alignment device of the present invention.

The alignment device includes a mounting mechanism that is adapted to be affixed to a prosthetic knee socket, mechanical knee or other prosthetic device. A prosthetic limb is operatively connected to the mounting mechanism and is adapted to move in forward and rearward directions in an anterior-posterior plane upon adjustment of the alignment device. An extendable and retractable positioning mechanism is operatively connected to the mounting mechanism and the prosthetic limb. The prosthetic limb is angularly aligned in the anterior-posterior plane upon extension and retraction of the positioning mechanism. The positioning mechanism may include a manually adjustable turnbuckle assembly, hydraulic actuator, electric actuator or other adjustment device that is readily accessible on the alignment device to permit adjustments by the wearer.

The alignment device of the present invention is intended to give the wearer more control and adaptability over the types of shoes that may be worn. The alignment device of the present invention provides the ability to change the loading on the knee socket in such a way that it provides less irritation to areas on or around the residual limb common to amputees. Moreover, the alignment device of the present invention gives the wearer a readily adjustable heel-to-toe configuration without disturbing any other fixed adjustments on the prosthetic limb, and without requiring adjustment tools.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 7 is a cross-sectional view taken along line 7—7 of FIG. 6 illustrating a slidable mount for the alignment device of the present invention;

FIG. 8 is view similar to FIG. 6 of an alignment device for a prosthetic limb in accordance with a fifth embodiment of the present invention, illustrating a linkage assembly as a positioning mechanism in the alignment device;

FIG. 9 is a cross-sectional view taken along line 9—9 of FIG. 8;

FIG. 12 is a partial perspective view of an alignment device for a prosthetic limb in accordance with an eighth embodiment of the present invention, illustrating a linkage assembly as a positioning mechanism in the alignment device;

FIG. 13 is a cross-sectional view taken along line 13—13 of FIG. 12;

FIG. 13A is an enlarged view of the linkage assembly illustrated in FIG. 13 in a locked position;

FIG. 13B is a view similar to FIG. 13A illustrating the linkage assembly in an unlocked position;

FIG. 14 is a view similar to FIG. 6 of an alignment device for a prosthetic limb in accordance with a ninth embodiment of the present invention, illustrating a linkage assembly as a positioning mechanism in the alignment device; and FIG. 15 is a cross-sectional view taken along line 15—15 of FIG. 14.

DETAILED DESCRIPTION OF SPECIFIC EMBODIMENTS

Figure 1:
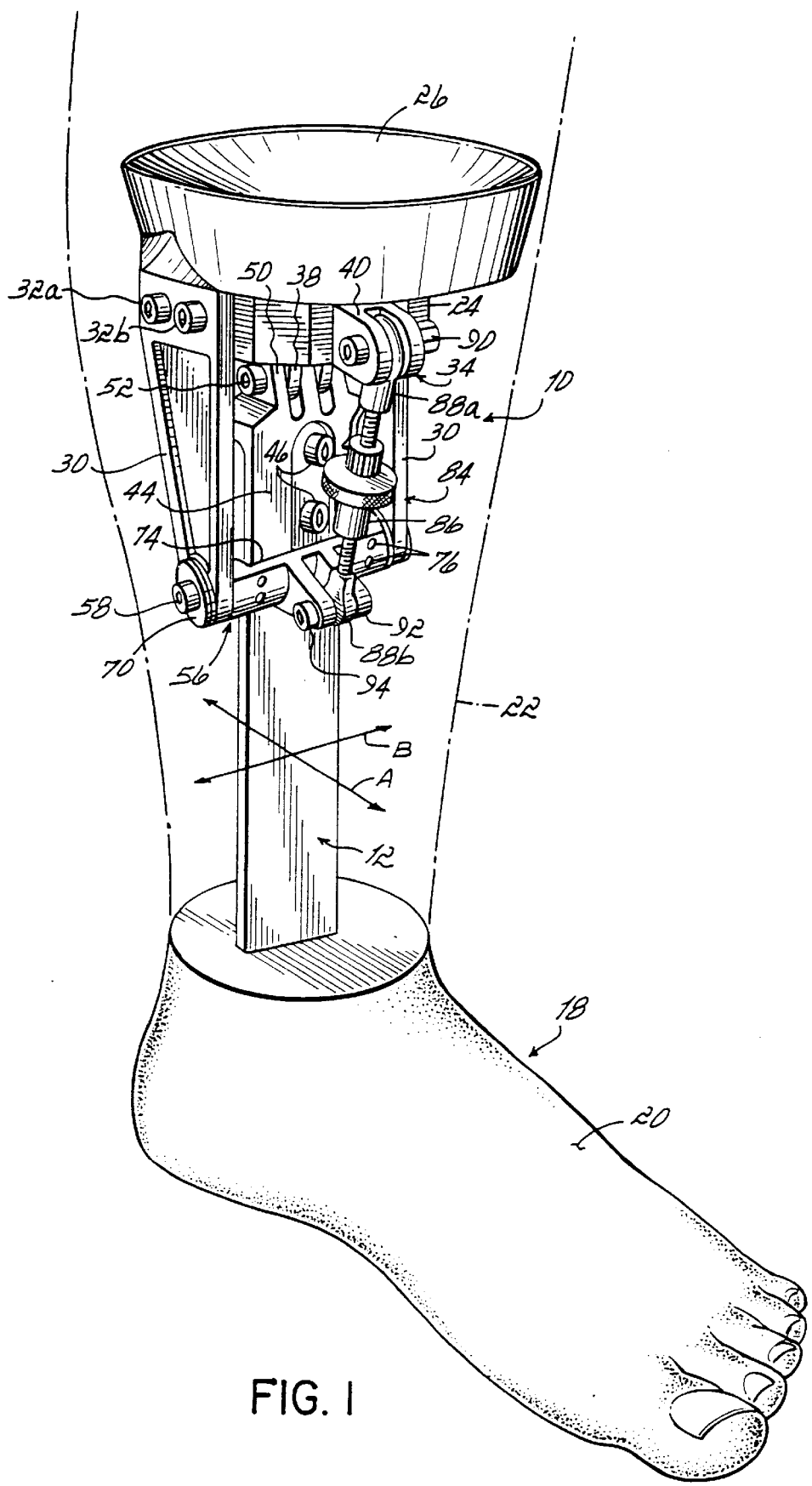
FIG. 1 is a perspective view of an alignment device for a prosthetic limb in accordance with one embodiment of the present invention, illustrating a turnbuckle assembly as a positioning mechanism in the alignment device.

With reference to the figures, and to FIGS. 1–4 in particular, one embodiment of an alignment device 10 for a prosthetic limb 12 is shown in accordance with the principles of the present invention. As will be described in greater detail below, alignment device 10 is particularly adapted to provide angular alignment of the prosthetic limb 12 in an anterior-posterior plane defined by axis "A" (FIG. 1) to optimize the toe-to-heel pitch and gait of the wearer as different shoes 14, 16 (FIGS. 2 and 3) with varying heel heights are worn.

As illustrated and described herein, prosthetic limb 12 may be a laminated plate-type prosthetic device similar to the lower limb prosthetic device sold under the trademark Flex Foot and described in U.S. Pat. Nos. 4,547,913 and 4,822,363 to Phillips, each disclosure of which is incorporated herein by reference in its entirety, although other types of prosthetic devices are also contemplated. A prosthetic foot 18, such as a leaf-spring foot 19 (FIG. 10) covered with a foot shell 20 (FIGS. 1–3), is connected to a lower end of the prosthetic limb 12. A shell cover 22 (shown in phantom in FIG. 1) that simulates the muscle tone of the wearer may be mounted about the prosthetic limb 12 as is well known in the art. While the present invention will be described herein in a below-the-knee amputation environment, those of ordinary skill in the art will readily appreciate the application of the present invention in combination with artificial or mechanical knees and other types of prosthetic devices without departing from the spirit and scope of the present invention.

Alignment device 10 includes a mounting base 24 that may be supported by a mounting adaptor 26 through a set of vertically aligned fasteners (not shown) that extend upwardly through the mounted base 24 and connect to the mounting adaptor 26. Alternatively, the mounting base 24 may be formed integrally with mounting adaptor 26. Mounting adaptor 26 may be a concave or cup-shaped support made from thermoset or thermoform plastic that is adapted to be connected to a conventional prosthetic socket 28 (FIGS. 2 and 3) as is well known in the art, with the alignment device 10 positioned below the prosthetic socket 28. A pair of side plates 30 are mounted on either side of the mounting base 24 through a pair of fasteners 32a, 32b that extend across the width of the mounting base 24 and through the side plates 30.

Figure 2:
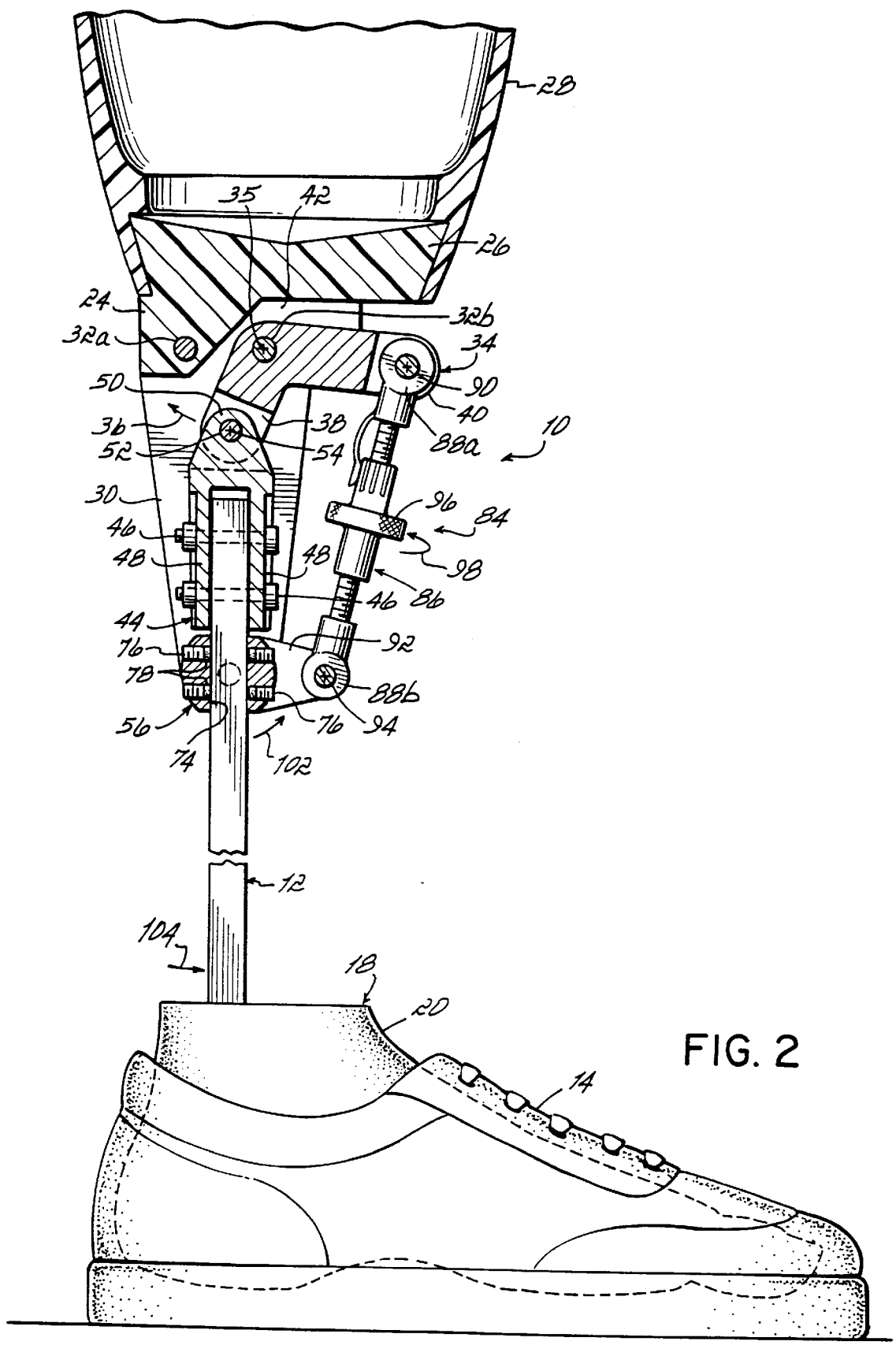
FIG. 2 is a side view, partially in cross-section, of the alignment device and prosthetic limb illustrated in FIG. 1.
Figure 3:
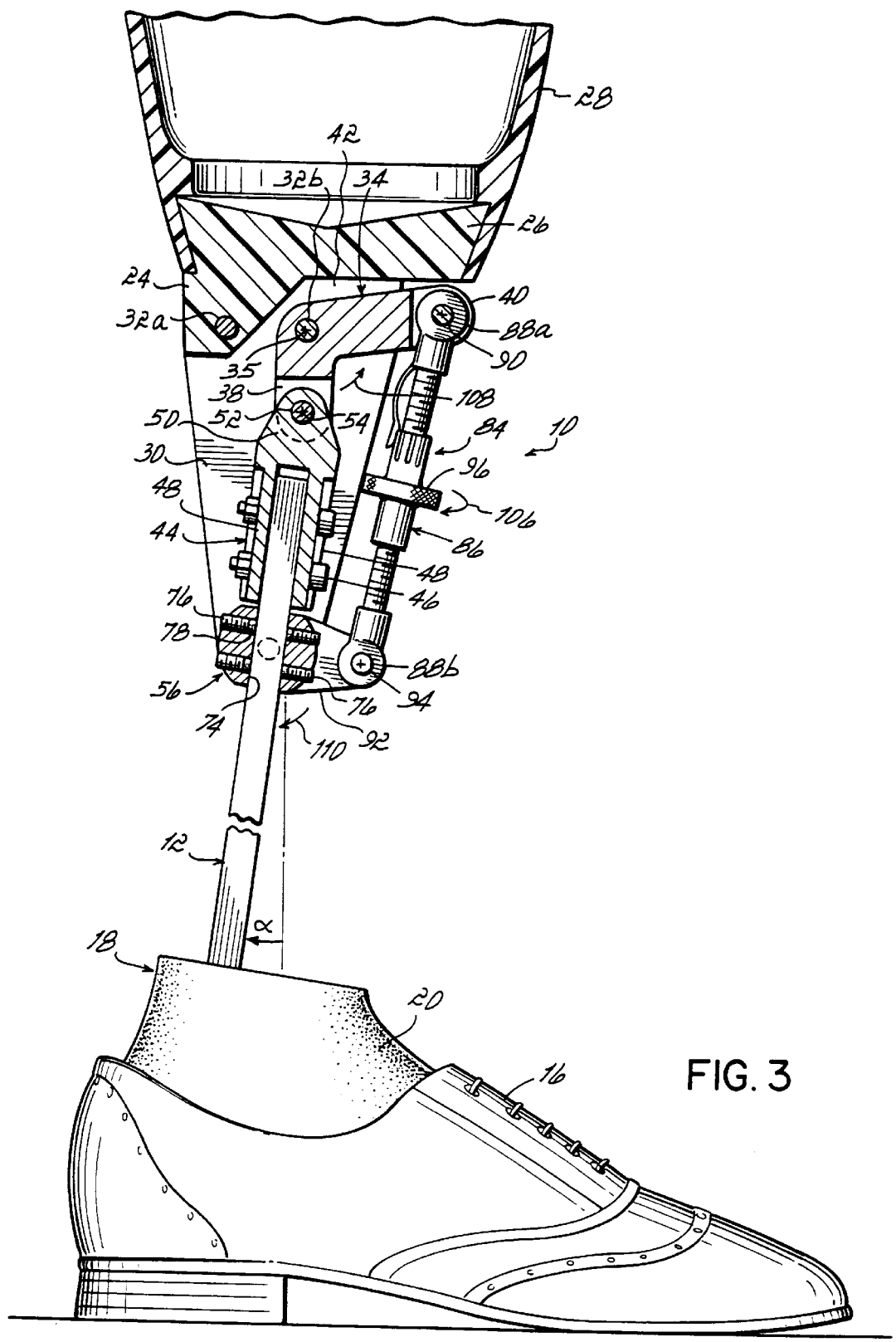
FIG. 3 is a view similar to FIG. 2 illustrating angular alignment of the prosthetic limb in an anterior-posterior plane upon actuation of the positioning mechanism.

As best understood with reference to FIGS. 2 and 3, a generally L-shaped linkage or lever 34 is pivotally mounted to one of the fasteners 32b for pivotal rotation about the fastener 32b in a plane defined by axis "A" (FIG. 1), as illustrated by arrow 36 in FIG. 2. The lever 34 is adapted to rotate about a hinge axis 35 defined by the fastener 32b. The lever 34 may terminate in a pair of U-shaped ends 38 and 40. The mounting base 24 has a recess 42 (FIGS. 2–4) for receiving the lever 34. A prosthetic limb support mechanism 44, such as a U-shaped clamp as illustrated in the figures, is mounted on an upper end of the prosthetic limb 12 through a pair of fasteners 46 that extend through legs 48 of the support mechanism 44 and the thickness of limb 12. Support mechanism 44 includes a hinge connection 50 that is pivotally connected to lever end 38 through a hinge pin 52 that extends through the hinge connection 50 and the lever end 38. The hinge connection 50 of support mechanism 44 is adapted to rotate about a hinge axis 54 defined by the hinge pin 52.

Prior to mounting the prosthetic limb 12 in support mechanism 44 through fasteners 46, the limb 12 is cut to an appropriate length for the particular wearer. During the fitting process, the prosthetic limb 12 may be moved laterally in the support mechanism 44 before final assembly to provide lateral adjustment of the limb 12 in the medial-lateral plane defined by axis "B" (FIG. 1). The prosthetic limb 12 may additionally be rotated in the medial-lateral plane during the fitting process to adjust the abduction-adduction angle of the limb 12 for a custom fit.

Further referring to FIGS. 1–4, a prosthetic limb receiving member 56 is rotatably mounted between the side plates 30. A pair of fasteners 58 are threadedly engaged in bores 59 in the ends 60 of receiving member 56. The ends 60 of the receiving member 56 are located in bushings 62 (FIG. 4), for example, nylon bushings, that extend through bores 64 formed at a lower end of the side plates 30. Inner ends 66 of the nylon bearings 62 engage ends 60 of the rotatable member 56, while outer ends 68 of the bearings 62 are clamped between washers 70 and an outer wall 72 of the side plates 30. Set screws 61 are also threadedly engaged in bores 59 below the fasteners 58.

Figure 4:
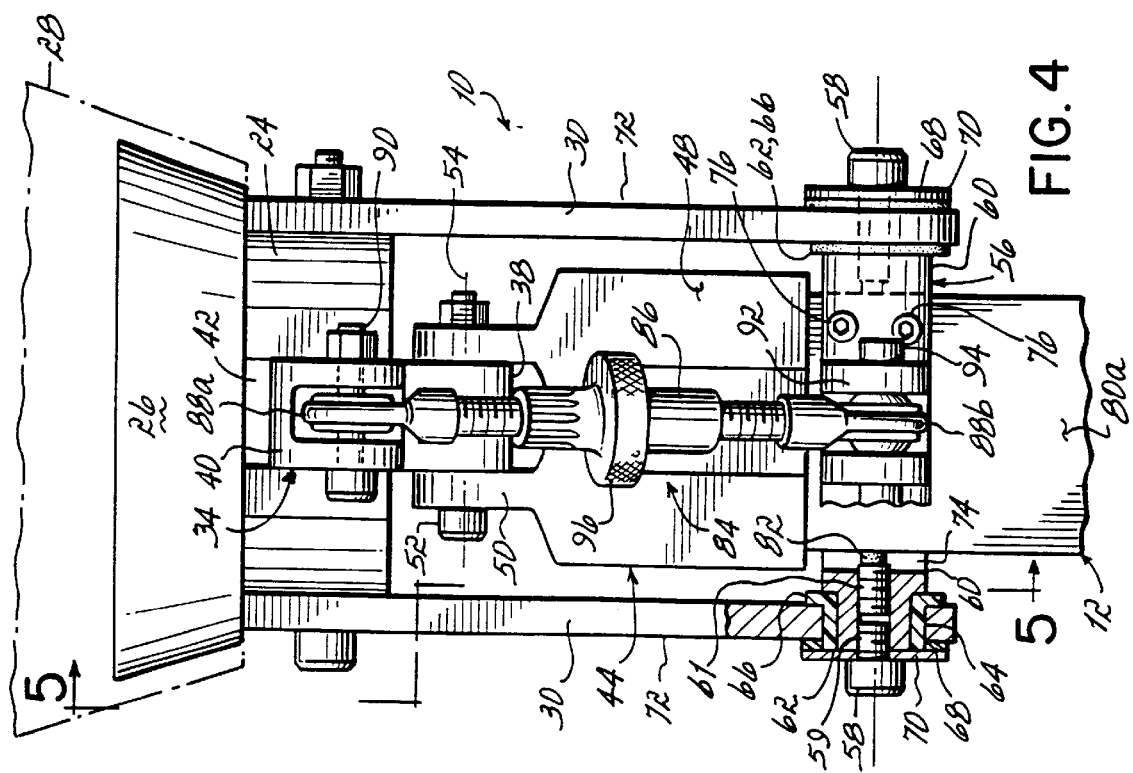
FIG. 4 is a partial front view of the alignment device illustrated in FIG. 1.

As best understood with reference to FIGS. 2–4, the rotatable member 56 includes an opening 74 extending through the member 56 for slidably receiving the prosthetic limb 12. Set screws 76 extend into the opening 74, and may include bearing tips 78 (FIG. 6), for example, nylon tips, that engage front and rear surfaces 80a, 80b of the prosthetic limb 12 to permit sliding movement of the limb 12 relative to the rotatable member 56. The set screws 76 are provided to prevent fore and aft movement of the prosthetic limb 12 in the opening 74. The set screws 59 may also include tips 82 (FIG. 4), for example, nylon tips, to permit sliding movement of the limb 12 relative to the rotatable member 56 while preventing lateral movement of limb 12 within the opening 74. It will be appreciated by those of ordinary skill in the art that other bearing structures are possible for permitting relative movement of the limb 12 and the rotatable member 56 without departing from the spirit and scope of the present invention. For example, one or more nylon bearing blocks or plates (not shown) may be provided within the opening 74 to slidably engage the prosthetic limb 12.

An expandable and retractable positioning mechanism or linkage 84, such as a turnbuckle assembly 86, includes hinge connections 88a, 88b formed at opposite ends the assembly 86. The upper hinge connection 88a of turnbuckle assembly 86 is pivotally connected to the lever end 40 through a pin 90, while the lower hinge connection 88b of turnbuckle assembly 86 is pivotally connected to an arm 92, which may be U-shaped, and extends outwardly from the rotatable limb receiving member 56 through a pin 94.

As those of ordinary skill in the art will readily appreciate, the turnbuckle assembly 86 is easily accessible for manual actuation by the wearer. As shown in FIG. 2, as turnbuckle wheel 96 is manually rotated in one direction, as represented by arrow 98, the turnbuckle assembly 86 retracts in a generally linear direction which simultaneously rotates lever 34 in a clockwise direction, as represented by arrow 36, and limb receiving member 56 in a counterclockwise direction, as represented by arrow 102. During retraction of turnbuckle assembly 56, the clockwise rotation of lever 34 moves the hinge connection 50 of limb support mechanism 44 in a clockwise direction as shown in FIG. 2 which results in a forward angular movement of the prosthetic limb 12 in the anterior-posterior plane, as represented by arrow 104. During this movement, the prosthetic limb 12 rotates generally about a horizontal axis defined by the limb receiving member 56. As the hinge connection 50 moves in the clockwise direction and the limb receiving member 56 rotates in a counterclockwise direction to provide angular movement of prosthetic limb 12 in the forward direction, the prosthetic limb 12 slides upwardly through the opening 74 formed in the rotatable limb receiving member 56. Movement of the prosthetic limb 12 in the forward direction may be desirable to accommodate a flat or low heel shoe, such as shoe 14 of FIG. 2.

As shown in FIG. 3, the heeled shoe 16 may require angular adjustment of the prosthetic limb 12 in a rearward direction in the anterior-posterior plane to optimize the toe-to-heel pitch and gait for the wearer. To accomplish the desired angular movement of limb 12, the turnbuckle wheel 96 is manually rotated in an opposite direction to that shown in FIG. 2, as represented by arrow 106. The turnbuckle assembly 86 extends in a generally linear direction which simultaneously rotates lever 34 in a counterclockwise direction, as represented by arrow 108, and limb receiving member 56 in a clockwise direction, as represented by arrow 110. During extension of turnbuckle assembly 86, the counterclockwise rotation of lever 34 moves the hinge connection 50 of limb support mechanism 44 in a counterclockwise direction as shown in FIG. 3 which results in a rearward angular movement of the prosthetic limb 12 in the anterior-posterior plane, as represented by angle "a". It will be appreciated that as the hinge connection 50 moves in the counterclockwise direction and limb receiving member 56 moves in a clockwise direction to provide angular movement of prosthetic limb 12 in the rearward direction, the prosthetic limb 12 slides downwardly through the opening 74 formed in the rotatable limb receiving member 56. It will also be appreciated that as the prosthetic limb 12 is moved in forward and rearward angular movements, the rotatable limb receiving member 56 acts as a general hinge or fulcrum about which the prosthetic limb 12 rotates during the forward and rearward angular adjustments. In this way, the prosthetic foot 18 is advantageously maintained generally below the prosthetic socket 28 during the full range of motion of the alignment device 10.

Figure 5:
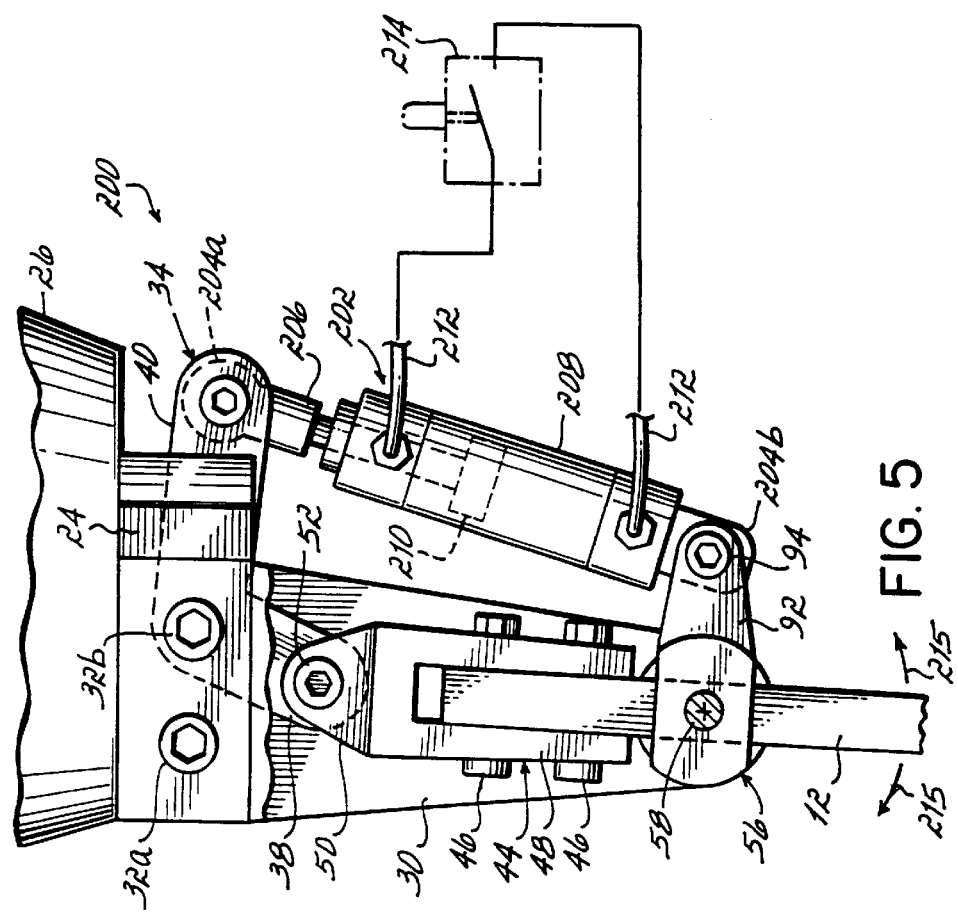
FIG. 5 is a partial side view taken on lines 5—5 of FIG. 4 of an alignment device for a prosthetic limb in accordance with a second embodiment of the present invention, illustrating a hydraulic actuator as a positioning mechanism in the alignment device.

As shown in FIG. 5, an alignment device 200 in accordance with an alternative embodiment of the present invention is illustrated for providing angular alignment of prosthetic limb 12, where like reference numerals are used to identify like parts. In this embodiment, the turnbuckle assembly 86 of FIGS. 1–4 is replaced with an extensible and retractable hydraulic actuator 202 that includes hinge connections 204a, 204b formed at opposite ends of the actuator 202. One hinge connection 204a is connected to a moveable end of piston rod 206 and rotatably connected to lever end 40, while the other hinge connection 204b extends outwardly from an opposite end of actuator housing 208 and is rotatably connected to connection 92 of rotatable limb receiving member 56. The actuator 202 is filled with hydraulic fluid that is free to port to opposite sides of piston head 210 through fluid lines 212 and a manually actuatable switch 214. While the switch 214 is manually depressed, the wearer is able to manually adjust the angular position of the prosthetic limb 12, as represented by arrows 215. When the desired angular position of limb 12 is achieved, the switch 214 may be released to set the limb 12 in the desired adjusted angular position. Switch 214 may be mounted on one of the side plates 30 or any other suitable area.

Figure 5A:
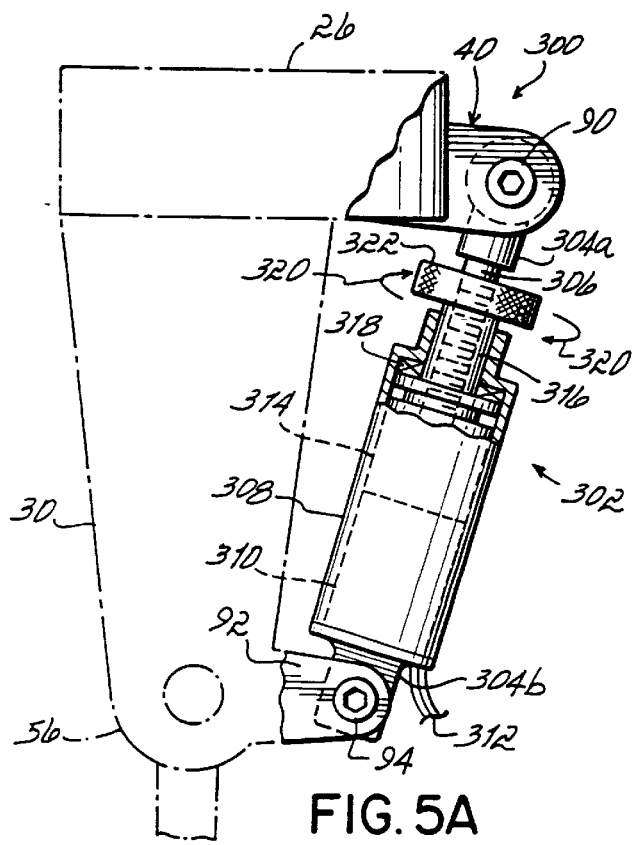
FIG. 5A is a view similar to FIG. 5 of an alignment device for a prosthetic limb in accordance with a third embodiment of the present invention, illustrating an electric actuator as a positioning mechanism in the alignment device.

Alternatively, an alignment device 300 in accordance with another embodiment of the present invention is shown in FIG. 5A, where like reference numerals represent like parts. In this embodiment, the turnbuckle assembly 86 of FIGS. 1–4, and the hydraulic actuator 202 of FIG. 5, may be replaced with an extendable and retractable electric actuator 302. Actuator 302 includes hinge connections 304a, 304b formed at opposite ends of the actuator wherein one hinge connection 304a is connected to a moveable threaded shaft 306 and rotatably connected to lever end 40, while the other hinge connection 304b extends outwardly from an opposite end of actuator housing 308 and is rotatably connected to connection 92 of rotatable limb receiving member 56. The actuator 302 includes a reversible electric motor 310 coupled to a power source (not shown) and manually actuatable switch (not shown) through electrical leads 312, and a planetary gear drive 314 connected to a mechanical output of the electric motor 310. The planetary gear drive 314 is connected to a threaded collar 316 that rotates when the motor 310 is energized upon actuation of a switch (not shown) coupled to the motor. A bearing 318 is provided within the actuator housing 308 to permit rotation of the collar 316 within the housing. It will be appreciated that rotation of the threaded collar 316 in opposite directions, as represented by arrows 320, retracts or extends the moveable threaded shaft 306 relative to the actuator housing 308. An actuatable wheel 322 is connected to the threaded collar 316 to permit manual rotation of the collar 316 as desired to retract or extend the moveable threaded shaft 306.

Figure 6:
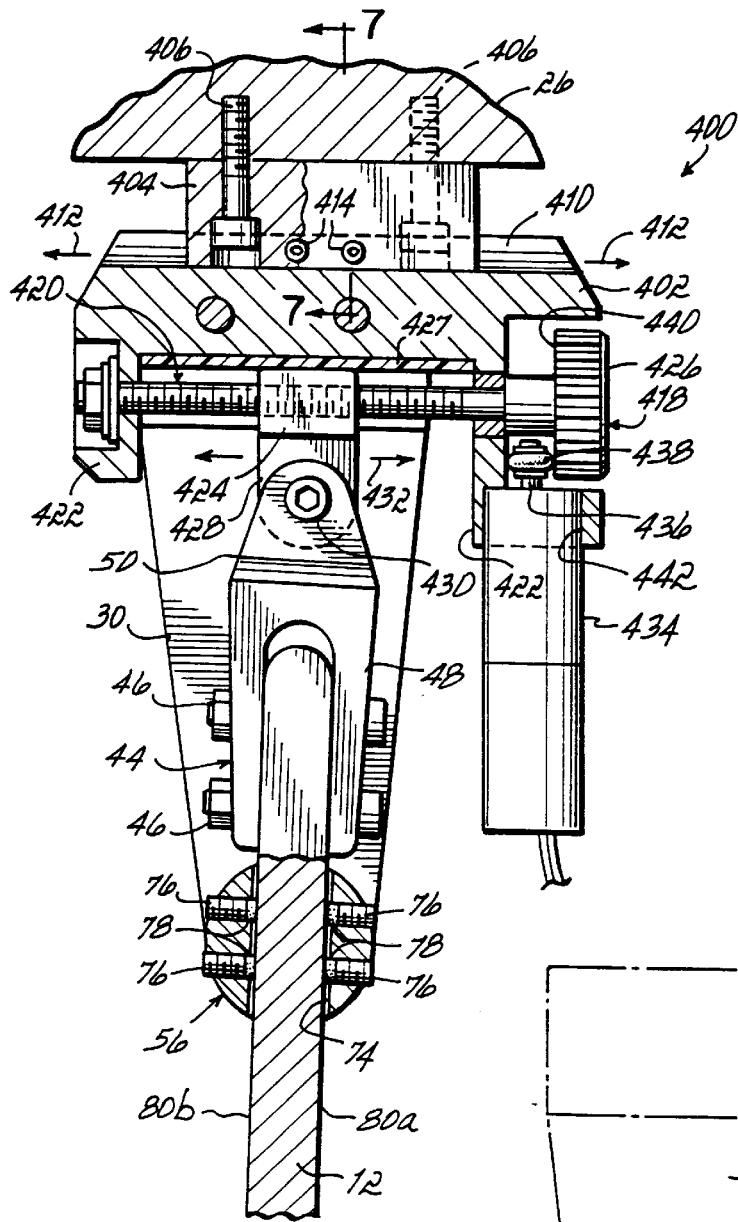
FIG. 6 is a partial cross-sectional view of an alignment device for a prosthetic limb in accordance with a fourth embodiment of the present invention, illustrating a linkage assembly as a positioning mechanism in the alignment device.

As shown in FIGS. 6–7, an alternative embodiment of an alignment device 400 in accordance with the principles of the present invention is shown, where like reference numerals are used to identify like parts. Alignment device 400 includes a mounting base 402 that is slidably mounted to mounting adaptor 26 through an adjustable mount 404. Adjustable mount 404 is connected to mounting adaptor 26 through a set of vertically aligned fasteners 406 that extend upwardly through the adjustable mount 404 and connect to the mounting adaptor 26. As shown in FIG. 7, a lower end of adjustable mount 404 may include an elongated dovetail groove 408 that extends generally parallel to the anterior-posterior plane. An upper end of the mounting base 402 may include a dovetail tongue 410 that cooperates with the dovetail groove 408 formed in the mounting adaptor 26. With this arrangement, the position of the alignment device 400 may be adjusted in forward and rearward directions relative to the mounting adaptor 26, as represented by arrows 412 (FIG. 6), to adjust the toe pressure exerted on the prosthetic foot 18 (FIG. 1) of the wearer. After the desired forward or rearward adjustment of alignment device 400 is achieved, the mounting base 402 is fixed to the adjustable mount 404 through a set of horizontally aligned set screws 414 that extend through bores 416 (FIG. 7) formed in the adjustable mount 404 and engage the dovetail tongue 410 of the mounting base 402. While a dovetail mounting arrangement is shown, those of ordinary skill in the art will appreciate that other structural formations and configuration of components is possible without departing from the spirit and scope of the present invention.

With further reference to FIGS. 6–7, an extendable and retractable positioning mechanism 418, arranged as a linkage assembly, is provided to move the prosthetic limb 12 through the forward and rearward angular movements described in detail above. The positioning mechanism 418 includes a threaded screw 420 rotatably connected to a pair of flanges 422 of the alignment device 400. The threaded screw 420 extends across the length of the mounting base 402 and is aligned generally parallel to the anterior-posterior plane. A pair of spaced guide pins (not shown) are also connected to the pair of flanges 422 and extend across the length of the alignment device 400 on opposite sides of the threaded screw 420.

As best understood with reference to FIG. 6, a generally T-shaped coupling member 424 is threadably connected to the threaded screw 420 for extended and retracted movement along the screw 420 upon manual rotation of actuation wheel 426. A nylon bearing plate 427 is mounted between the coupling member 424 and the mounting base 402 to permit relative movement between the components. Coupling member 424 includes a pair of unthreaded bores (not shown) that slidably receive the pair of guide pins (not shown). The coupling member 424 includes a hinge connection 428, which may be U-shaped, and is rotatably connected with the hinge connection 50 formed on an upper end of the limb support mechanism 44 through a pin 430. Those of ordinary skill in the art will readily appreciate that as the adjustment wheel 426 is rotated in opposite directions, the coupling member 424 will be extended or retracted on the threaded screw shaft 420, as represented by arrows 432 (FIG. 6) to angularly align the prosthetic limb 12 as discussed in detail above. The rotatable limb receiving member 56 permits the prosthetic limb 12 to slide through the opening 74 during the adjustment process.

An electric actuator 434, for example, a motor and planetary gear drive, may be mounted to one of the flanges 422 for rotating the actuation wheel 426 when the motor (not shown) within the actuator 434 is energized. A spindle 436 is connected to the actuator 434 and includes an elastomeric O-ring 438 positioned about one end of the spindle 436. The O-ring 438 is adapted to engage a surface 440 of the actuation wheel 426 for rotating the wheel 426 when the motor (not shown) is energized. When the electric actuator 434 is not used, an optional filler piece (not shown) is inserted in the motor receiving bore 442 formed in one of the flanges 422.

Referring now to FIGS. 8–9, an alignment device 500 in accordance with an alternative embodiment of the present invention is illustrated where like reference numerals are used to identify like parts. In this embodiment, an extendable and retractable positioning mechanism 502, arranged as a linkage assembly, is provided to move the prosthetic limb 12 through forward and rearward angular movements. The positioning mechanism 500 includes a threaded screw 504 that is pivotally mounted in a rotatable pin 506. Pin 506 is rotatably connected to a hinge connection 508, which may be U-shape, and hinge connection 508 is integral with mounting base 510. Screw 504 includes an unthreaded shank portion 512 extending through an unthreaded bore 514 formed in the rotatable pin 506. Stop collars 516 are mounted on screw 504 on opposite sides of pin 506 to prevent lateral movement of the screw 504. The threaded screw 504 extends across the length of the adjustment device 500 and is aligned generally parallel to the anterior-posterior plane.

As best understood with reference to FIGS. 8 and 9, a coupling member 518, in the form of a rotatable pin, is connected to the threaded screw 504 through a threaded bore 520 for extended and retracted movement along the screw 504 upon manual rotation of actuation wheel 522. Limb support mechanism 524 includes a hinge connection 526, which may be U-shaped, for rotatably supporting the coupling member 518 in a pair of nylon bushings 528 inserted into upstanding legs 530 of the support mechanism 524. A stop collar 531 is affixed to the free end of threaded screw 504 to prevent the coupling member 518 from moving off the end of screw 504.

As best understood with reference to FIG. 8, a limb receiving member 532 is rotatably supported between the pair of side plates 30 (one shown). In this embodiment, the prosthetic limb 12 is received in an opening 534 formed in the rotatable member 532, and a pair of fasteners 536 (one shown) extend through the rotatable member 532 and the thickness of the limb 12 to rigidly fix the limb 12 in the rotatable member 532. It will be appreciated that as the coupling member 518 is extended and retracted on threaded screw 504, as represented by arrows 538 (FIG. 8), the threaded screw 504, pin 506, coupling member 518 and limb receiving member 532 rotate to permit the desired forward or rearward angular alignment of the prosthetic limb 12.

Figure 10:
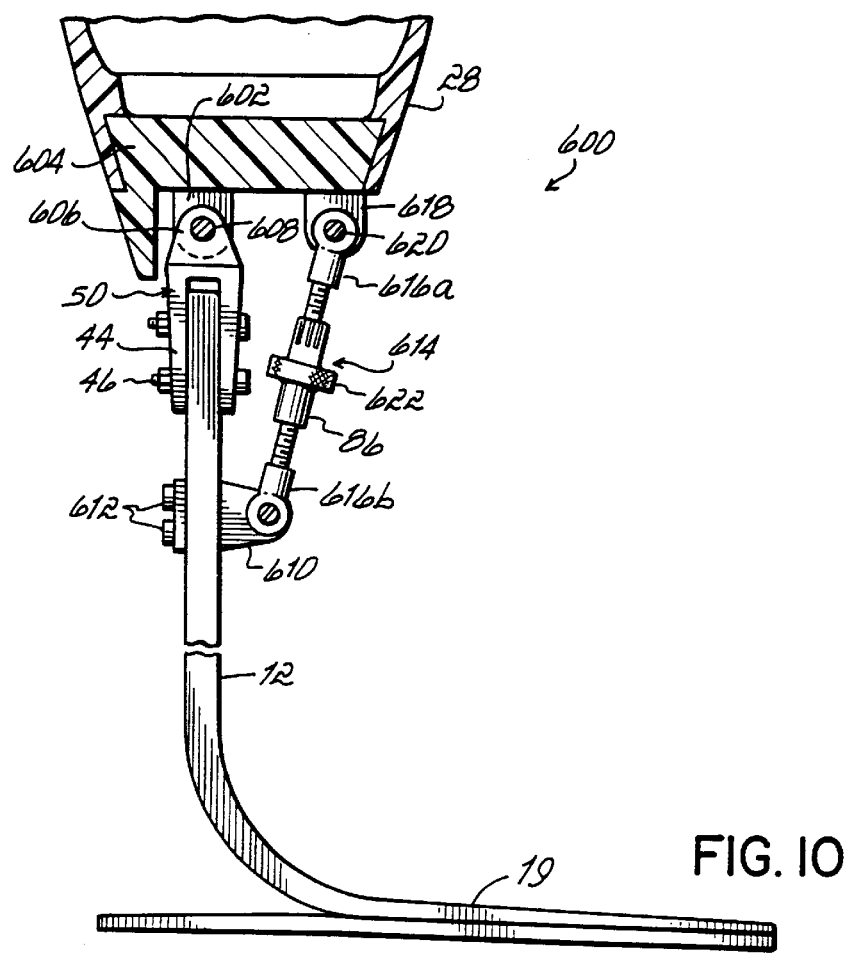
FIG. 10 is view similar to FIG. 2 of an alignment device for a prosthetic limb in accordance with a sixth embodiment of the present invention, illustrating a turnbuckle assembly as a positioning mechanism in the alignment device.

With reference now to FIG. 10, an alternative embodiment of an alignment device, designated at numeral 600, is shown in accordance with the principles of the present invention. In this embodiment, alignment device 600 includes a mounting mechanism 602 that is mounted to a mounting adaptor 604. The mounting mechanism 602 includes a hinge connection 606, which may be U-shaped, and thus, hinge mechanism 602 is rotatably connected to the hinge connection 50 formed on the upper end of the limb support mechanism 44 through a pin 608. A hinge connection 610, which may be U-shaped, is mounted to the prosthetic limb 12 through a pair of fasteners 612.

An expandable and retractable positioning mechanism or linkage 614, such as turnbuckle assembly 86, includes hinge connections 616a, 616b formed at opposite ends the turnbuckle assembly 86. The upper hinge connection 616a of turnbuckle assembly 86 is pivotally connected to a hinge connection 618, which may be U-shaped. Hinge connection 618 is mounted to mounting adaptor 604. A pin 620 extends through the hinge connections 616a and 618 to permit rotation of hinge connection 616a relative to the fixed hinge connection 618. Lower hinge connection 616b is rotatably connected to hinge connection 610. It will be appreciated that rotation of manually actuatable wheel 622 in opposite directions will retract or extend the turnbuckle assembly 86 as discussed in detail above to cause the prosthetic limb 12 to move in forward and rearward angular movements through rotation of the limb 12 about pin 608. While turnbuckle assembly 86 is shown, it will be appreciated that the hydraulic actuator 202 or electric actuator 302 may be used as well.

Figure 11:
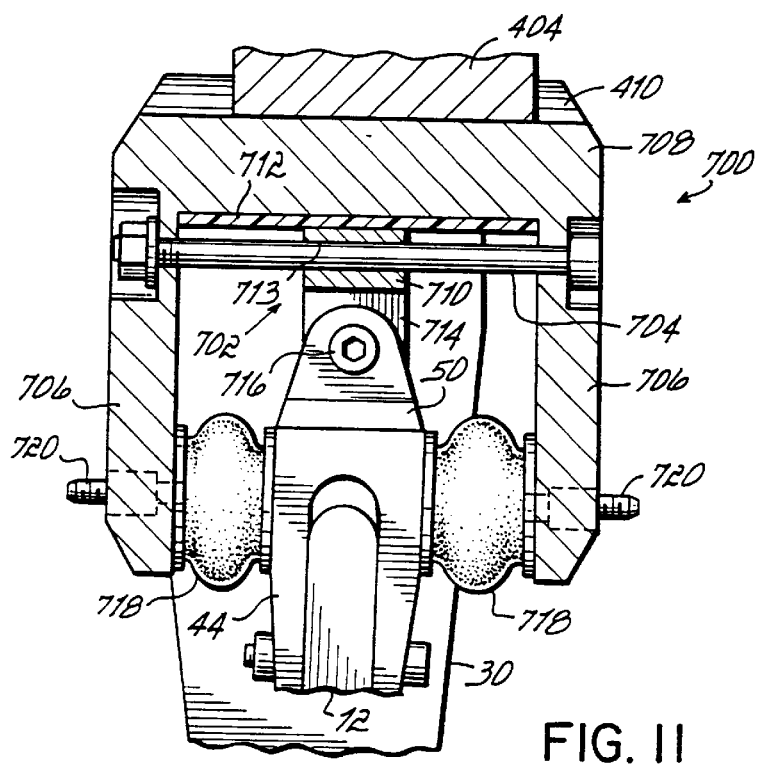
FIG. 11 is a view similar to FIG. 6 of an alignment device for a prosthetic limb in accordance with a seventh embodiment of the present invention, illustrating a linkage assembly as a positioning mechanism in the alignment device.

Referring now to FIG. 11, an alignment device 700 in accordance with an alternative embodiment of the present invention is illustrated. An extendable and retractable positioning mechanism 702, arranged as a linkage assembly, is provided to move the prosthetic limb 12 through forward and rearward angular movements as desired by the wearer. The positioning mechanism 702 includes a shaft 704 connected to a pair of flanges 706 of a mounting base 708. The shaft 704 extends across the length of the mounting base 708 and is aligned generally parallel to the anterior-posterior plane.

A generally T-shaped coupling member 710 is slidably mounted on the shaft 704 for extended and retracted movement along the shaft. A pair of spaced guide pins (not shown) are also connected to the pair of flanges 706 and extend across the length of alignment device 700 on opposite sides of the shaft 704. A nylon bearing plate 712 is mounted between the coupling member 710 and the mounting base 708 to permit relative movement between the components. Coupling member 710 includes three unthreaded bores 713 (one shown) that slidably receive shaft 704 and the pair of guide pins (not shown). Coupling member 710 includes a hinge connection 714 which may be U-shaped, and thus, coupling member 710 is rotatably connected with the hinge connection 50 formed on an upper end of the limb support mechanism 44 through a pin 716. A pair of selectively inflatable pneumatic bladders 718 are positioned on opposite sides of the limb 12 between the flanges 706 and the limb support mechanism 44. The bladders 718 may be held in place by a threaded fastener (not shown) extending through the support mechanism 44 and terminating in the bladders 718. The bladders 718 are manually inflatable and deflatable through valve stems 720 which are also used to support the bladders on their outer ends. Alternatively, the bladders 718 may receive hydraulic fluid, in which case a manually actuatable switch (not shown), such as switch 214 of FIG. 5, may be incorporated to permit porting of hydraulic fluid between the pair of bladders 718. Those of ordinary skill in the art will readily appreciate that as each bladder 718 is selectively inflated or deflated through valve stems 720, the coupling member 710 will be extended or retracted on the shaft 704 to angularly align the prosthetic limb 12 as discussed in detail above. The rotatable limb receiving member 56 (FIG. 1) permits the prosthetic limb 12 to slide through the opening 74 (FIG. 4) during the adjustment process.

With reference now to FIGS. 12, 13, 13A and 13B, an alternative embodiment of an alignment device 800 in accordance with the principles of the present invention is shown, where like numerals are used to identify like parts. In this embodiment, an extendable and retractable positioning mechanism 802, arranged as a linkage assembly, is provided to move a pylon-shaped prosthetic limb 804 through the forward and rearward angular movements as described in detail above. The positioning mechanism 802 includes a pair of shafts 806 connected to a pair of flanges 808 provided on a mounting base 810. The shafts 806 extend across the length of the mounting base 810 and are aligned generally parallel to the anterior-posterior plane.

A generally T-shaped coupling member 812 is slidably mounted on the shafts 806 for extended and retracted movement along the shafts. Coupling member 812 includes a pair of unthreaded bores 814 (one shown in dash lines in FIGS. 13A and 13B) that slidably receive the pair of shafts 806. Coupling member 812 includes a hinge connection 816 which may be U-shaped, and thus, coupling member 812 is rotatably connected with a hinge connection 818 formed on an upper end of a limb support mechanism 820. As best understood with reference to FIG. 13, limb support mechanism 820 terminates in a socket 822 that is received within an adaptor 824 mounted on the upper end of the pylon-shaped prosthetic limb 804. Four (4) set screws 826 are provided to securely mount the adaptor 824 to the socket 822.

As best understood with reference to FIGS. 12 and 13, a limb receiving member 828 is rotatably supported between the pair of side plates 30 through a pair of fasteners 830. The ends of the limb receiving member 828 are located in bushings 834 (FIG. 12), for example nylon bushings, that extend through bores 836 (one shown in dash in FIG. 13) formed at a lower end of the side plates 30. Limb receiving member 828 includes a spherically-shaped-bushing 838 that is mounted within a spherically-shaped socket 840 of the rotatable limb receiving member 828. Bushing 838 may be snap-fit into the socket 840 and is held in place by a locking ring 842 that threadably engages with the rotatable limb receiving member 828. The rotatable limb receiving member 828 includes an opening extending through the member 828 for slidably receiving the prosthetic limb 804.

Further referring to FIGS. 12–13, a locking mechanism 846 is mounted within the mounting base 810 that is operable to engage gear teeth 848 formed on an upper surface of the coupling member 812 to prevent sliding movement of the coupling member 812 on the pair of shafts 806. Locking mechanism 846 includes a rack gear support 850 having a top wall 852 and a pair of opposite flanges 854 that depend from the top wall 852 to define a rack gear receiving recess 856. A rack gear 858 is positioned between the pair of flanges 854 in the recess 856 so that the rack gear 858 is movable in opposite vertical directions, but is prevented from moving in a horizontal direction by the pair of flanges 854. The rack gear 854 includes gear teeth 860 that are operable to engage the gear teeth 848 formed on the coupling member 812 when the rack gear 858 is lowered into engagement with the coupling member 812 as described in detail below.

The locking mechanism 846 further includes a pair of spaced cam plates 862 that extend on opposite longitudinal sides of the rack gear 858 and are mounted to a button actuator 864. The cam plates 862 and button actuator 864 are spring-biased relative to the rack gear support 850 through a spring or other suitable biasing member 866. The pair of cam plates 862 include a series of cam apertures 868 that receive pins 870 extending from opposite longitudinal sides of the rack gear 858.

As shown in FIG. 13A, the cam plates 862 are biased to cause the rack gear 858 to engage the coupling member 812 to prevent sliding movement of the coupling member 812 on the pair of shafts 806. Upon manual depression of the button actuator 864 as shown in FIG. 13B, the cam plates 862 are translated relative to the rack gear support 850 to cause the rack gear 858 to raise vertically in the receiving recess 856 and out of engagement with the coupling member 812.

As those of ordinary skill in the art will readily appreciate, the button actuator 864 is easily accessible for manual actuation by the wearer. As the button 864 is manually depressed, the rack gear 858 retracts, i.e., raises vertically, within the recess 856 and the wearer is then free to set the angular alignment of the prosthetic limb 804 to a comfortable setting. Thereafter, the button actuator 864 is released and the rack gear 858 is then forced into engagement with the coupling member 812 to lock and set the angular position of the prosthetic limb 804 as desired by the wearer.

With reference now to FIGS. 14 and 15, an alignment device 900 in accordance with yet another alternative embodiment of the present invention is illustrated. An extendable and retractable positioning mechanism 902, arranged as a linkage assembly, is provided to move the prosthetic limb (not shown) through forward and rearward angular movements as desired by the wearer. The positioning mechanism 902 includes a pair of shafts 904 (one shown in FIG. 14) connected to a pair of flanges 906 provided on a mounting base 908. The shafts 904 extend across the length of the mounting base 908 and are aligned generally parallel to the anterior-posterior plane.

A generally T-shaped coupling member 910 is slidably mounted on the shafts 904 for extended and retracted movement along the shafts 904. Coupling member 910 includes a pair of unthreaded bores 911 that slidably receive the pair of shafts 904, and a slotted or keyed shaft 912 that is threadably connected to and extends from the coupling member 910 in a direction generally parallel to the shafts 904. The slotted shaft 912 includes multiple annular discs 914 that extend radially outwardly from the shaft 912 to define locking slots 916 between each pair of the discs 914. Coupling member 910 further includes a hinge connection 918, which may be U-shaped, to rotatably connect the coupling member 910 with a hinge connection 920 formed on an upper end of a limb support mechanism 922 as described in detail above.

Further referring to FIGS. 14 and 15, a locking mechanism 924 is mounted within the mounting base 908 that is operable to engage the slotted shaft 912 extending from the coupling member 910 to prevent sliding movement of the coupling member 910 on the pair of shafts 904. In particular, locking mechanism 924 includes a spring-biased locking plate 926 that is positioned to move in a transverse direction relative to the slotted shaft 912 of the coupling member 910. The locking plate 926 includes an enlarged aperture 928 having a diameter greater than that of the annular discs 914 formed on the slotted shaft 912, and a smaller aperture 930 communicating with the enlarged aperture 928 that has a diameter less than that of the annular discs 914. The locking plate 926 is mounted to or integral with a button actuator 932 so that the locking plate 926 is spring-biased relative to the mounting base 908 through a spring or other suitable biasing member 934.

As shown in FIG. 15, the locking plate 926 is biased to cause the locking plate 926, and in particular the smaller aperture 930, to engage between a pair of the annular discs 914 on the slotted shaft 912 to prevent sliding movement of the coupling member 910 on the pair of shafts 904. Upon manual depression of the button actuator 932, the locking plate 926 is translated relative to the slotted pin 912 so that the enlarged aperture 928 is moved in registry with the slotted pin 912. In this released position, the coupling member 910 is free to slidably move along the pair of shafts 904 to change the angular position of the prosthetic limb (not shown).

As those of ordinary skill in the art will readily appreciate, the button actuator 932 is also easily accessible for manual actuation by the wearer. When the button 932 is manually depressed, the slotted shaft 912 is disengaged from the locking plate 926, and the wearer is then free to set the angular alignment of the prosthetic limb (not shown) to a comfortable setting. Thereafter, the button actuator 932 is released and the locking plate 926 is then moved into engagement with the slotted pin 912 to prevent the coupling member 910 from slidably moving on the pair of shafts 904 to lock and set the angular position of the prosthetic limb (not shown) as desired by the wearer.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicant's general inventive concept.

Having described the invention, what is claimed is:

1. An alignment device for a below-the-knee prosthetic lower leg adapted to be operatively connected to a prosthetic foot, comprising:
   a mounting mechanism having a base and a pivotal connection and being configured to be operatively connected to the below-the-knee prosthetic lower leg through the pivotal connection proximate an upper end of the prosthetic lower leg, the pivotal connection being movable in a path relative to the base so that the prosthetic lower leg is adapted to move angularly in an anterior-posterior plane relative to the base; and
   an extendable and retractable positioning mechanism operatively connected to the mounting mechanism and configured to be operatively connected to the prosthetic lower leg, whereby the positioning mechanism is adapted to angularly align the prosthetic lower leg in the anterior-posterior plane upon extension or retraction of the positioning mechanism.

2. The alignment device of claim 1 wherein the positioning mechanism is extendable and retractable at least partially in a generally linear direction.

3. The alignment device of claim 1 further including a below-the-knee prosthetic lower leg operatively connected proximate an upper end thereof to the mounting mechanism.

4. The alignment device of claim 3 further including a prosthetic foot operatively connected at a lower end of the prosthetic lower leg.

5. The alignment device of claim 1 further including a prosthetic socket operatively connected to the mounting mechanism.

6. The alignment device of claim 1 wherein the positioning mechanism comprises a turnbuckle assembly.

7. The alignment device of claim 1 wherein the positioning mechanism comprises a hydraulic actuator.

8. The alignment device of claim 1 wherein the positioning mechanism comprises an electric actuator.

9. The alignment device of claim 1 wherein the positioning mechanism comprises a linkage assembly including a threaded screw and a coupling member threadably mounted on the screw and operatively connected to the prosthetic lower leg.

10. The alignment device of claim 1 wherein the positioning mechanism comprises a linkage assembly including a shaft and a coupling member slidably mounted on the shaft and operatively connected to the prosthetic lower leg.

11. The alignment device of claim 10 further comprising a locking mechanism associated with the coupling member and operable to prevent sliding movement of the coupling member on the shaft.

12. The alignment device of claim 11 wherein the locking mechanism comprises a rack gear having a plurality of teeth operable to engage a plurality of teeth formed on the coupling member.

13. The alignment device of claim 11 wherein the locking mechanism comprises a locking plate operable to engage a slotted pin associated with the coupling member.

14. The alignment device of claim 10 further including at least one inflatable bladder member operable to move the coupling member along the shaft.

* * * * *